(12) United States Patent
Filippini et al.

(10) Patent No.: US 7,968,530 B2
(45) Date of Patent: Jun. 28, 2011

(54) ORGANIC DERIVATIVES, THEIR SALTS AND USE FOR THE CONTROL OF PHYTOPATHOGENS

(75) Inventors: Lucio Filippini, Novara (IT); Marilena Gusmeroli, Monza (IT); Silvia Mormile, Novara (IT); Luigi Mirenna, Milan (IT)

(73) Assignee: Isagro S.p.A, Milan (IT)

( * ) Notice: Subject to any disclaimer, the term of this patent is extended or adjusted under 35 U.S.C. 154(b) by 212 days.

(21) Appl. No.: 12/086,906

(22) PCT Filed: Dec. 15, 2006

(86) PCT No.: PCT/EP2006/012428
§ 371 (c)(1),
(2), (4) Date: Jul. 24, 2008

(87) PCT Pub. No.: WO2007/071428
PCT Pub. Date: Jun. 28, 2007

(65) Prior Publication Data
US 2009/0029948 A1 Jan. 29, 2009

(30) Foreign Application Priority Data

Dec. 22, 2005 (IT) .............................. MI2005A2459

(51) Int. Cl.
*A61K 31/66* (2006.01)
*C07C 215/00* (2006.01)
(52) U.S. Cl. ............ 514/114; 514/667; 564/503; 564/15
(58) Field of Classification Search ................. 514/114, 514/667; 564/503, 15
See application file for complete search history.

(56) References Cited

U.S. PATENT DOCUMENTS

| 3,355,485 A | 11/1967 | Shah |
| 3,759,980 A | 9/1973 | Rosen et al. |
| 4,849,438 A | 7/1989 | Iriuchijima et al. |
| 5,776,915 A | 7/1998 | Peterson et al. |
| 2002/0064955 A1 | 5/2002 | Lee et al. |

FOREIGN PATENT DOCUMENTS

| DE | 101 17 805 A1 | 10/2002 |
| EP | 0 156 729 A | 10/1985 |
| EP | 0 812 821 A1 | 12/1997 |
| GB | 2 018 776 A | 10/1979 |
| GB | 2 132 887 A | 7/1984 |
| JP | 2005-264149 A | 9/2005 |
| WO | WO 99/32704 A | 7/1999 |
| WO | WO 2004/024159 A | 3/2004 |

OTHER PUBLICATIONS

Mulvihill et al., 2001, CAS: 135:380503.*
Anon's, 1965, CAS: 63:34778.*
Foley et al., 1980, CAS: 93:245515.*
Hioki et al., 1995, CAS: 123: 135902.*
Banasiak et al., 1992, CAS: 116: 53509.*
Yamamoto et al., 1991, CAS: 115: 28235.*
Banasiak et al., 1988, CAS: 109:2469.*
Gamburyan et al., 1975, CAS: 82: 170245.*
Rouvier E et al.," Amines Presentant un Autre Groupment Fonctionnel", Bull. Soc. Chime de France, 1971, pp. 171701723.
Hayashi Y. et al, "Preparation of Tertiary Amines Having Different Substitutents From Quaternary 2-Hydroxyethyl Ammonium Salts", J.Jpn.Oil Chem. Soc., 1967,vol. 36, pp. 409-412.
H.M.Mehendale et al., Phosphatidyl Carnitine, Nature, 1966,vol. 211, pp. 759-761.
A.Jezierski, "Increeased Intensity of Tert-Butoxyl Radical Emission in 4-Chloro-2-Methylphenoxyacetic Acid Synthesis" Pestic Sci, vol. 55, 1999, pp. 1229-1232.
A.Grun et al., "Uber Salze Der Phosphatid-Basen", Ber.Der Deutschen Chem. Ges., vol. 59b, 1926, pp. 1345-1350.
O.Spivey et al., "Conductance Study", J. Phy. Chem., 1964,Vcol. 68, No. 8, pp. 2126-2130.
H.T.Clarke et al., "The Action of Formaldehyde on Amines and Amino Acids", J.A.C.S., vol. 55, 1933, pp. 4571-4587.
PCT Search Report, Dated Oct. 10, 2007.

* cited by examiner

*Primary Examiner* — Rei-tsang Shiao
(74) *Attorney, Agent, or Firm* — Hedman & Costigan, P.C.; James V. Costigan

(57) ABSTRACT

Organic compounds are described, which are capable of forming quaternary salts, quaternary salts thereof with a structure having general formula (I) and their use for the control of phytopathogen fungi.

32 Claims, No Drawings

ORGANIC DERIVATIVES, THEIR SALTS AND USE FOR THE CONTROL OF PHYTOPATHOGENS

The present invention relates to organic compounds capable of forming quaternary salts, the relative quaternary salts and the relative use for the control of phytopathogens.

Quaternary salts are compounds known for being soluble in both hydrophilic and lyophilic environments. An example of a quaternary salt is represented by choline, an ubiquitous substance in nature, known for being a biostimulating compound for plants as described in T G. Mason, G. Blunden (1989) Bot. Mar. 32 313-316.

Choline, moreover, in the interior of plants, is easily oxidized to glycine betaine.

In the agronomical field, when administered, for example, to fruit plants, glycine betaine contributes to controlling abiotic and nutritional growth stress, reducing imperfections in fruit rinds and the tendency of the rind to break during ripening, as described in EP-A-0806897, by acting as an osmolyte regulator.

The Applicant has now surprisingly found that various organic compounds capable of forming quaternary salts and quaternary salts thereof have an unexpected activity as fungicidal and bactericidal products in the agronomical field, and obtain a prolonged protective action on vegetables with respect to phytopathogen fungi and bacteria.

These compounds are also capable of effectively synergizing with numerous other active principles known for having a fungicidal activity or, in turn, capable of inducing the natural defense of plants so as to be able to control both biotic and abiotic stress.

An object of the present invention therefore relates to organic compounds having general formula (I),

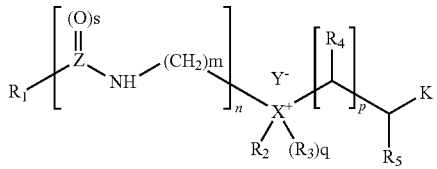
(I)

wherein:
K represents a $CH_2OH$ or $COOR_a$ group;
$R_a$ represents a linear or branched $C_1$-$C_{26}$ alkyl group optionally substituted;
$R_1$ represents a hydrogen or a linear or branched $C_1$-$C_{26}$ alkyl group optionally substituted; a linear or branched $C_1$-$C_{26}$ haloalkyl group optionally substituted; a linear or branched $C_1$-$C_{26}$ alkoxyl group optionally substituted; a linear or branched $C_1$-$C_{26}$ alkylthio group optionally substituted; a linear or branched $C_2$-$C_{26}$ alkenyl group optionally substituted; a linear or branched $C_2$-$C_{26}$ alkinyl group optionally substituted; a $C_3$-$C_{30}$ cycloalkyl group optionally condensed or a condensed $C_{17}$ cycloalkyl group of the steroid type optionally substituted; a $C_3$-$C_{30}$ cycloalkoxyl group optionally condensed and optionally substituted; a heterocyclic group optionally substituted; an aryl group optionally substituted; a heteroaryl group optionally, substituted; a linear or cyclic $C_6$-$C_{12}$ group of the saccharide type optionally substituted; a $C_1$-$C_{26}$ alkylamine group or a $C_2$-$C_{26}$ dialkylamine group optionally substituted for n different from 0;

$R_2$ and $R_3$, the same or different, represent a $C_1$-$C_3$ alkyl group optionally substituted;
$R_4$ and $R_5$, the same or different, represent a hydrogen atom, or a linear or branched $C_1$-$C_6$ alkyl group optionally substituted; a linear or branched $C_2$-$C_6$ alkenyl group optionally substituted; a $C_3$-$C_6$ cycloalkyl group optionally substituted; a hydroxyl group; an aryl group optionally substituted; a heteroaryl group optionally substituted; a heterocyclic group optionally substituted;
$R_4$ and $R_5$ can individually form a cycle together with $R_2$;
X represents a nitrogen or sulfur atom;
Z represents a carbon or sulfur atom;
m represents a number ranging from 1 to 5;
n and p represent a number ranging from 0 to 3;
q has the value of 0 for X=sulfur or the value of 0 or 1 for X=nitrogen;
Y, when q has the value of 0 for X=sulfur and when q has the value of 1 for X=nitrogen, represents a halide, such as Cl$^-$, Br$^-$; a nitrate anion (NO$_3^-$), a nitrite anion (NO$_2^-$); a phosphate anion selected from $H_2PO_4^-$, $HPO_4^{-2}$, $PO_4^{-3}$; a phosphite anion selected from $H_2PO_3^-$, $HPO_3^{-2}$, $PO_3^{-3}$; a carbonate anion (CO$_2^{-2}$); a bicarbonate anion (HCO$_3^-$); a sulfate anion (SO$_4^{-2}$); a hydrogen-sulfated anion (HSO$_4^-$); or Y represents the salicylate anion; the acetylsalicylate anion; the saccharinate anion; the 3-aminobutanoate anion; the cyclamate anion; the taurinate anion; the ethylphosphonate anion; or Y is absent when q has the value of 0 for X=nitrogen;
s has the value of 1 for Z=carbon or the value of 2 for Z=sulfur.

The Applicant has also found that the compounds having general formula (I), not only have a direct fungicidal and bactericidal action, but are also capable of stimulating the natural defense systems of plants and inducing resistance in the plants themselves; this method for controlling diseases is becoming of growing interest as it is based on the amplification of a natural process already present in plants by the application of these compounds.

The Applicant has also surprisingly found that these compounds having general formula (I) are also an optimum means of controlling phytopathogens in genetically modified vegetable species to amplify the original natural defenses.

A further object of the present invention is therefore the use of compounds having general formula (I):

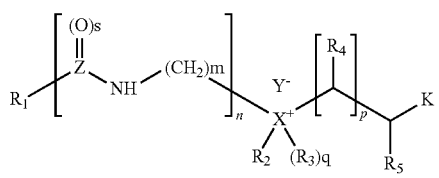
(I)

wherein:
K represents a $CH_2OH$ or $COOR_a$ group;
$R_a$ represents a linear or branched $C_1$-$C_{26}$ alkyl group optionally substituted;
$R_1$ represents a hydrogen or a linear or branched $C_1$-$C_{26}$ alkyl group optionally substituted; a linear or branched $C_1$-$C_{26}$ haloalkyl group optionally substituted; a linear or branched $C_1$-$C_{26}$ alkoxyl group optionally substituted; a linear or branched $C_1$-$C_{26}$ alkylthio group optionally substituted; a linear or cyclic $C_2$-$C_{26}$ alkenyl group optionally substituted; a linear or branched $C_2$-$C_{26}$ alkinyl group optionally substituted; a $C_3$-$C_{30}$ cycloalkyl group optionally condensed or a condensed $C_{17}$ cycloalkyl group of the steroid type optionally substituted; a $C_3$-$C_{30}$ cycloalkoxyl group optionally condensed and optionally substituted; a heterocyclic group optionally substituted; an aryl group optionally substituted; a heteroaryl group optionally substituted; a linear or cyclic $C_6$-$C_{12}$ group of the saccharide type optionally substituted; a $C_1$-$C_{26}$ alkylamine group or a $C_2$-$C_{26}$ dialkylamine group optionally substituted for n different from 0;

$R_2$ and $R_3$, the same or different, represent a $C_1$-$C_3$ alkyl group optionally substituted;

$R_4$ and $R_5$, the same or different, represent a hydrogen atom, or a linear or branched $C_1$-$C_6$ alkyl group optionally substituted; a linear or branched $C_2$-$C_6$ alkenyl group optionally substituted; a $C_3$-$C_6$ cycloalkyl group optionally substituted; a hydroxyl group; an aryl group optionally substituted; a heteroaryl group optionally substituted; a heterocyclic group optionally substituted;

$R_4$ and $R_5$ can individually form a cycle together with $R_2$;

X represents a nitrogen or sulfur atom;

Z represents a carbon or sulfur atom;

m represents a number ranging from 1 to 5;

n and p represent a number ranging from 0 to 3;

q has the value of 0 for X=sulfur or the value of 0 or 1 for X=nitrogen;

Y, when q has the value of 0 for X=sulfur and when q has the value of 1 for X=nitrogen, represents a halide, such as $Cl^-$, $Br^-$; a nitrate anion ($NO_3^-$), a nitrite anion ($NO_2^-$); a phosphate anion selected from $H_2PO_4^-$, $HPO_4^{-2}$, $PO_4^{-3}$; a phosphite anion selected from $H_2PO_3^-$, $HPO_3^{-2}$, $PO_3^{-3}$; a carbonate anion ($CO_2^{-2}$); a bicarbonate anion ($HCO_3^-$); a sulfate anion ($SO_4^{-2}$); a hydrogen-sulfate anion ($HSO_4^-$); or Y represents the salicylate anion; the acetylsalicylate anion; the saccharinate anion; the 3-aminobutanoate anion; the cyclamate anion; the taurinate anion; the ethylphosphonate anion; or Y is absent when q has the value of 0 for X=nitrogen;

s has the value of 1 for Z=carbon or the value of 2 for Z=sulfur, for the control of phytopathogen fungi and bacteria.

In particular an object of the present invention relates to the use of compounds with a structure having general formula (I) for the control of phytopathogen fungi and bacteria by stimulating the natural defense systems of plants and the induction of resistance in the plants themselves.

In particular, the use of the compounds having general formula (I) for the control of phytopathogen fungi is curative and/or preventive.

A $C_1$-$C_{26}$ alkyl group, refers to a linear or branched $C_1$-$C_{26}$ alkyl group, optionally substituted by one or more substituents, the same or different.

Examples of this group are: methyl, ethyl, propyl, isopropyl, butyl, isobutyl, tert-butyl, capryl, lauryl, stearyl, eicosyl, hexacosyl.

A $C_1$-$C_{26}$ haloalkyl group refers to a linear or branched alkyl group, substituted by one or more halogen atoms, the same or different.

Examples of this group are: fluoromethyl, difluoromethyl, trifluoromethyl, trichloromethyl, 2,2,2-trifluoroethyl, 2,2,2-trichloroethyl, 2,2,3,3-tetrafluoropropyl, 2,2,3,3,3-pentafluoropropyl, perfluorooctanyl, perfluorododecyl.

A $C_1$-$C_{26}$ alkoxyl group refers to a $C_1$-$C_{26}$ alkoxyl group, wherein the aliphatic portion is a $C_1$-$C_{26}$ alkyl group, as previously defined.

Examples of this group are: methoxyl, ethoxyl, isopropoxyl, cyclopropylmethoxyl, lauryloxyl.

A $C_1$-$C_{26}$ thioalkyl group refers to a $C_1$-$C_{26}$ thioalkyl group, wherein the aliphatic portion is a $C_1$-$C_{26}$ alkyl group, as previously defined.

Examples of this group are: thiomethyl, thioethyl, thiolauryl, thiocapryl.

A $C_2$-$C_{26}$ alkenyl group refers to a linear or branched $C_2$-$C_{26}$ alkenyl group, optionally substituted by one or more substituents, the same or different.

Examples of this group are: ethenyl, propenyl, butenyl, 1-decenyl, 8-heptadecenyl, 8,11,14-heptadecatrienyl, 8,11-heptadecadienyl.

A $C_2$-$C_{26}$ alkinyl group refers to a linear or branched $C_2$-$C_{26}$ alkinyl group, optionally substituted by one or more substituents, the same or different.

Examples of this group are: ethinyl, propargyl, 1-dodecinyl, 1-octadecinyl.

A $C_3$-$C_{30}$ cycloalkyl group optionally condensed refers to a cycloalkyl group whose ring consists of 3-30 carbon atoms, optionally substituted by one or more substituents, the same or different.

Examples of this group are: cyclopropyl, 2,2-dichlorocyclopropyl, cyclobutyl, cyclopentyl, cyclohexyl, decaline, abietyl.

A condensed $C_{17}$ cycloalkyl group of the steroid type refers to a steroid group consisting of 17 carbon atoms, optionally substituted by one or more substituents, the same or different.

Examples of this group are: cholanyl, or chenodeoxycholanyl, or ursodeoxycholanyl, or deoxycholanyl, or iodeoxycholanyl, or lithocholanyl.

A $C_3$-$C_{30}$ cycloalkoxyl group refers to a $C_3$-$C_{30}$ cycloalkoxyl group wherein the aliphatic portion is a $C_3$-$C_{30}$ cycloalkyl group as previously defined.

Examples of this group are: cyclopentoxy, cyclohexyloxy, cholesteryl.

A $C_1$-$C_{26}$ alkylamine or a $C_2$-$C_{26}$ dialkylamine group refers to an alkylamine or dialkylamine group wherein the aliphatic portion is respectively a $C_1$-$C_{26}$ or two $C_1$-$C_{13}$ alkyl groups as previously defined.

Examples of this group are: methylamine, dimethylamine, ethylamine, isopropylamine, dibutylamine, dioctylamine, hexadecylamine, didecylamine.

An aryl group refers to an carbocyclic aromatic group optionally substituted by one or more groups, the same or different.

Examples of this group are: phenyl, naphthyl, phenanthryl.

A heteroaryl group refers to a penta- or hexa-atomic heterocyclic aromatic group also benzocondensed or heterobicyclic, containing from 1 to 4 heteroatoms selected from nitrogen, oxygen, sulfur, optionally substituted by one or more groups, the same or different.

Examples of hetero-aryl groups are: pyridine, pyrimidine, pyridazine, pyrazine, triazine, tetrazine, quinoline, quinoxaline, quinazoline, furan, thiophene, pyrol, oxazole, thiazole, isoxazole, isothiazole, oxadiazole, thiadiazole, pyrazole, imidazole, triazole, tetrazole, indole, benzofuran, benzothiophene, benzoxazole, benzothiazole, benzoxadiazole, benzothiadiazole, benzopyrazole, benzimidazole, benzotriazole, triazolepyridine, triazolepyrimidine, thiazoletriazole, cumarin.

A heterocyclic group refers to a saturated or unsaturated ring with three to twelve terms, containing at least a heteroatom selected from nitrogen, oxygen, sulfur, optionally condensed with another aromatic or nonaromatic ring.

Examples of heterocyclic rings are: pyrrolidine, piperidine, dihydropyridine, piperazine, 2,6-diketopiperazine, 2-ketoazetidine, morpholine, thiazine, indoline.

A linear or cyclic $C_6$-$C_{12}$ group of the saccharide type refers to a carbohydrate group in open or closed form.

Examples of this group are: gluconyl, glucopyranosyl, β-D-fructofuranosyl-α-D-glucopyranosyl, 4-O-β-D-galactopyranosyl-D-glucosyl.

Optionally substituted means, in all parts of the patent application, one or more substituents, the same or different, selected from the following groups: halogen atoms; $C_1$-$C_6$ alkyls, $C_1$-$C_6$ alkoxyls and $C_1$-$C_6$ alkylthio, in turn optionally substituted by halogen atoms; $C_1$-$C_6$ alkylcarbonyls and $C_1$-$C_6$ alkoxycarbonyls, optionally halogenated; aminocarbonyls, $C_1$-$C_6$ alkylaminocarbonyls, $C_2$-$C_{12}$ dialkylaminocarbonyls, optionally halogenated; carboxyl; $C_1$-$C_6$ alkylcarbonyloxy optionally halogenated; cyano; nitro; formyl; hydroxyl; amino; aryl and heteroaryl optionally substituted.

Examples of compounds having general formula (I), when q has the value of 0 for X=nitrogen, which are interesting for their activity are:
  N,N-dimethylethanolamine;
  3-dimethylamine-1-propanol;
  N-ethyl,N-methylethanolamine;
  2-dimethylaminopropanol;
  N-lauryl,N-methylethanolamine;
  methyl ester of N,N-dimethyl-β-alanine;
  methyl ester of N,N-dimethylglycine.

Examples of compounds having general formula (I) when q has the value of 0 for X=sulfur and the value of 1 for X=nitrogen, which are interesting for their activity are:
  Acid choline phosphite;
  Neutral choline phosphite;
  Choline ethylphosphonate;
  Acid laurylcholine phosphite;
  Neutral laurylcholine phosphite;
  Acid cocamidopropylcholine phosphite;
  Neutral cocamidopropylcholine phosphite;
  Acid stearylcholine phosphite;
  Neutral stearylcholine phosphite;
  Acid cholesterylcarbonylamidopropylcholine phosphite;
  Neutral cholesterylcarbonylamidopropylcholine phosphite;
  Acid cholanylamidopropylcholine phosphite;
  Neutral cholanylamidopropylcholine phosphite;
  Acid chenodeoxycholanylamidopropylcholine phosphite;
  Neutral chenodeoxycholanylamidopropylcholine phosphite;
  Acid N,N-dimethyl,N-laurylamidopropyl[L]valinol phosphite;
  Neutral N,N-dimethyl,N-laurylamidopropyl[L]valinol phosphite;
  Acid N,N-dimethyl,N-lauryl[L]valinol phosphite;
  Neutral N,N-dimethyl,N-lauryl[L]valinol phosphite;
  Acid N-lauryl,N-methyl[L]2-pyrrolidinemethanol phosphite;
  Neutral N-lauryl,N-methyl[L]2-pyrrolidinemethanol phosphite;
  Choline salicylate;
  Choline acetylsalicylate;
  Choline saccharinate;
  Choline cyclamate;
  Choline taurinate;
  Laurylcholine salicylate;
  Laurylcholine acetylsalicylate;
  Laurylcholine saccharinate;
  Laurylcholine cyclamate;
  Laurylcholine taurinate;
  Laurylcholine ethylphosphonate;
  Cocamidopropylcholine salicylate;
  Cocamidopropylcholine acetylsalicylate;
  Cocamidopropylcholine saccharinate;
  Cocamidopropylcholine cyclamate;
  Cocamidopropylcholine taurinate;
  Cocamidopropylcholine ethylphosphonate;
  Stearylcholine salicylate;
  Stearylcholine acetylsalicylate;
  Stearylcholine saccharinate;
  Stearylcholine cyclamate;
  Stearylcholine taurinate;
  Cholanylamidopropylcholine salicylate;
  Cholanylamidopropylcholine acetylsalicylate;
  Cholanylamidopropylcholine saccharinate;
  Cholanylamidopropylcholine cyclamate;
  Cholanylamidopropylcholine taurinate;
  Choline carbonate;
  Choline bicarbonate;
  Laurylcholine carbonate;
  Laurylcholine bicarbonate;
  Cocamidopropylcholine carbonate;
  Cocamidopropylcholine bicarbonate;
  Stearylcholine carbonate;
  Stearylcholine bicarbonate;
  Choline sulfate;
  Choline chloride;
  Laurylcholine sulfate;
  Laurylcholine hydrogen-sulfate;
  Cocamidopropylcholine sulfate;
  Cocamidopropylcholine bromide;
  Stearylcholine sulfate;
  Stearylcholine chloride;
  Acid choline phosphate;
  Neutral choline phosphate;
  Acid laurylcholine phosphate;
  Neutral laurylcholine phosphate;
  Acid cocamidopropylcholine phosphate;
  Neutral cocamidopropylcholine phosphate;
  Acid Stearylcholine phosphate;
  Neutral Stearylcholine phosphate;
  Acid phosphite of the methyl ester of cocamidopropylbetaine;
  Neutral phosphite of the methyl ester of cocamidopropylbetaine;
  Acid phosphite of betaine cetyl ester;
  Neutral phosphite of betaine cetyl ester; Salicylate of the methyl ester of cocamidopropylbetaine;
  Acetylsalicylate of the methyl ester of cocamidopropylbetaine;
  Salicylate of betaine cetyl ester;
  Acetylsalicylate of betaine cetyl ester;
  Cyclamate of the methyl ester of cocamidopropylbetaine;
  Saccharinate of the methyl ester of cocamidopropylbetaine;
  Cyclamate of betaine cetyl ester;
  Saccharinate of betaine cetyl ester;
  Bicarbonate of the methyl ester of cocamidopropylbetaine;
  Chloride of the methyl ester of cocamidopropylbetaine;
  Acid phosphite of the methyl ester of cholanylamidopropylbetaine;
  Neutral phosphite of the methyl ester of cholanylamidopropylbetaine;
  Acid phosphite of the methyl ester of carnitine;
  Neutral phosphite of the methyl ester of carnitine;
  Salicylate of the methyl ester of carnitine;
  Acetylsalicylate of the methyl ester of carnitine;
  Saccharinate of the methyl ester of carnitine;
  Carnitine chloride.

Particularly preferred are quaternary salts having general formula (I) when Y represents the salicylate anion; the acetylsalicylate anion; the saccharinate anion; the 3-aminobutanoate anion; the cyclamate anion; the taurinate anion; the ethylphosphonate anion; or when Y represents a phosphite anion selected from $H_2PO_3^-$, $HPO_3^{-2}$, $PO_3^{-3}$, a halide anion or a bicarbonate anion ($HCO_3$—).

The Applicant has now surprisingly found that quaternary salts having formula (I), when Y represents a phosphite anion selected from $H_2PO_3^-$, $HPO_3^{-2}$, $PO_3^{-3}$, or the salicylate anion; the acetylsalicylate anion; the saccharinate anion; the 3-aminobutanoate anion; the cyclamate anion; the taurinate anion; the ethylphosphonate anion, have a surprisingly higher activity than that expected deriving from the anion, which is known in literature for having its own biological efficacy, and the relative quaternary cation, demonstrating the synergism between the ionic couple of compounds having general formula (I) when q has the value of 0 for X=sulfur and the value of 1 for X=nitrogen.

An unexpected synergic effect has therefore been found between the cationic component and anionic component of quaternary salts having formula (I) when Y represents a phosphite anion selected from $H_2PO_3^-$, $HPO_3^{-2}$, $PO_3^{-3}$, or the salicylate anion; the acetylsalicylate anion; the saccharinate anion; the 3-aminobutanoate anion; the cyclamate anion; the taurinate anion and q has the value of 0 for X=sulfur and the value of 1 for X=nitrogen.

When they are not commercial products, the compounds having general formula (I), when q has the value of 0 for X=nitrogen, can be easily obtained according to the methods described for example in Comprehensive Organic Transformations 1989, R. C. Larock, or in March's Advanced Organic Chemistry 2001 V$^a$ edition, M. B. Smith, J. March.

The compounds having formula (I), when q has the value of 0 for X=sulfur and the value of 1 for X=nitrogen, can be obtained with different synthetic methods according to the meaning of the anion Y.

When Y has the meaning of a $Cl^-$ e $Br^-$ anion, and when $R_1$ has the meanings defined above with the exclusion of a $C_1$-$C_{26}$ alkoxyl group, or a $C_1$-$C_{26}$ alkylthio group, or a $C_3$-$C_{30}$ cycloalkoxyl group, or a $C_1$-$C_{26}$ alkylamine group, or a $C_2$-$C_{26}$ dialkylamine group, the quaternary salts having formula (I) can be easily obtained according to the reaction scheme A for n different from 0 and according to the reaction scheme B for n=0:

Scheme A

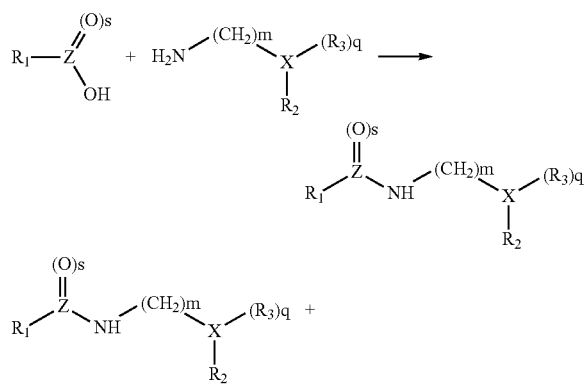

-continued

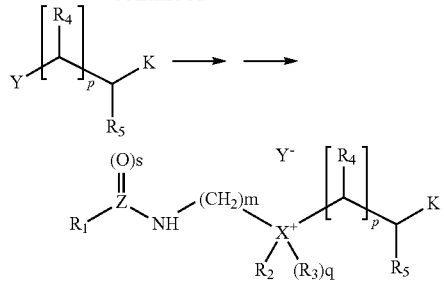

Scheme B

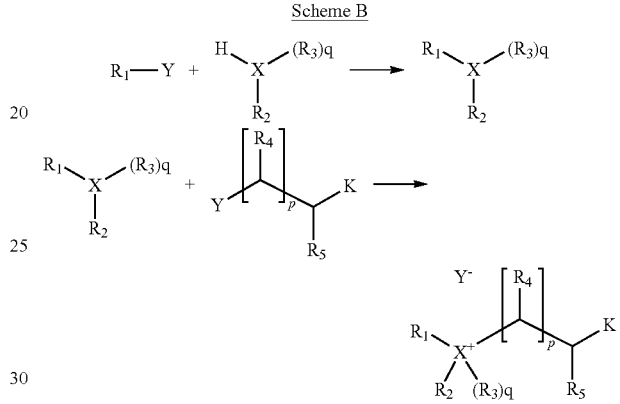

wherein K, $R_1$, $R_2$, $R_3$, $R_4$, $R_5$, X, Z, m, p, q and s have the meanings defined above and Y represents an outgoing group such as a chlorine atom or a bromine atom which also become the counterion of the final product.

The quaternary salts having general formula (I), according to reaction scheme A, for X=nitrogen, can be obtained by condensation of the suitable N',N'-dialkylamine-N-alkylamine or, for X=sulfur, by condensation of the suitable ω-alkylthioalkylamine with carboxylic acid of a suitable $R_1$ residue, and a condensing agent, optionally in the presence of a base in an organic or aqueous solvent, according to methods well known in the art, for example in Comprehensive Organic Transformations 1989, R. C. Larock, so as to form the corresponding amide.

The intermediate thus obtained is subsequently subjected to alkylation by reaction with the suitable halide, in water or in an organic solvent, at temperatures ranging from room temperature to 100° C., maintaining the pH at values of around 7.5, by the controlled addition of a solution of a strong base.

The quaternary salts having general formula (I), according to reaction scheme B, for X=nitrogen, can be obtained by alkylation of the suitable N',N'-dialkylamine-N-alkylamine or, for X=sulfur, by alkylation of the suitable ω-alkylthioalkylamine with the desired $R_1$ residue having the outgoing group Y, in the presence of a base in an organic or aqueous solvent, according to methods well known in the art, for example in Comprehensive Organic Transformations 1989, R. C. Larock, so as to form the corresponding tertiary amine.

The intermediate thus obtained is subsequently subjected again to alkylation by reaction with the suitable halide, in water or in an organic solvent, at temperatures ranging from room temperature to 100° C., maintaining the pH at values of around 7.5, by the controlled addition of a solution of a strong base.

The quaternary salts having formula (I), when Y has the meaning of a Cl⁻ and Br⁻ anion and when $R_1$ has the meanings of a $C_1$-$C_{26}$ alkoxyl group, or a $C_1$-$C_{26}$ alkylthio group, or a $C_3$-$C_{30}$ cycloalkoxyl group, or a $C_1$-$C_{26}$ alkylamine group, or a $C_2$-$C_{26}$ dialkylamine group, can be easily obtained according to the reaction scheme C for n different from 0:

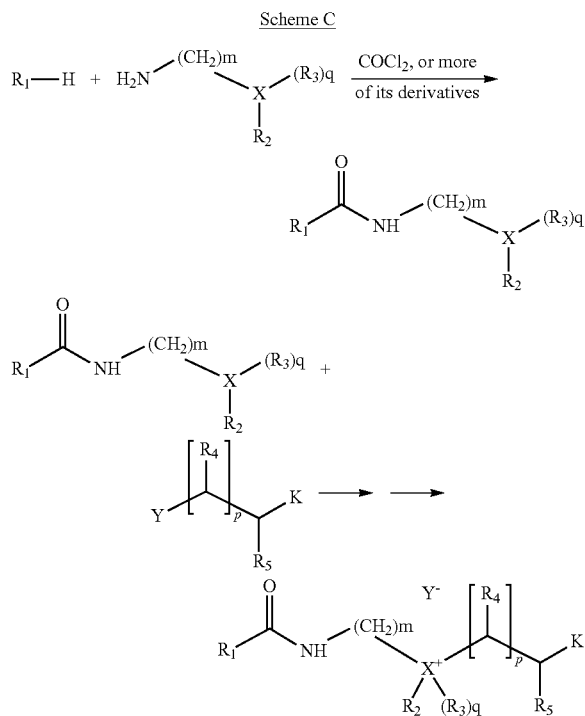

wherein K, $R_1$, $R_2$, $R_3$, $R_4$, $R_5$, X, Z, m, p, q and s have the meanings defined above and Y represents an outgoing group such as a chlorine atom or a bromine atom, which becomes the counterion of the final product.

The quaternary salts having general formula (I), according to reaction scheme C, for X=nitrogen, can be obtained by reaction of the suitable N',N'-dialkylamine-N-alkylamine or, for X=sulfur, by reaction of the suitable ω-alkylthioalkylamine with the desired $R_1$ residue having an alcoholic, or thioalcoholic, or aminic function when $R_1$ has the meanings of a $C_1$-$C_{26}$ alkoxyl group, or a $C_3$-$C_{30}$ cycloalkoxyl group, or a $C_1$-$C_{26}$ alkylthio group, or a $C_1$-$C_{26}$ alkylamine group, or a $C_2$-$C_{26}$ dialkylamine group respectively, in the presence of phosgene or one of its functional substitutes, such as, for example, diphosgene, triphosgene, 1,1'-carbonyldiimidazole, in an organic or aqueous solvent, according to methods well known in the art, for example in Comprehensive Organic Transformations 1989, R. C. Larock, so as to form the corresponding carbamate, thiocarbamate or urea.

The intermediate thus obtained is subsequently subjected again to alkylation by reaction with the suitable halide, in water or in an organic solvent, at temperatures ranging from room temperature to 100° C., maintaining the pH at values of around 7.5, by the controlled addition of a solution of a strong base.

When Y has a meaning different from a Cl⁻ and Br⁻ anion, the quaternary salts having formula (I) can be easily obtained by the exchange of the alkaline salts, such as for example sodium and potassium, of the suitable acids YH, with the halides of the quaternary cations synthesized as described above, according to the reaction scheme D:

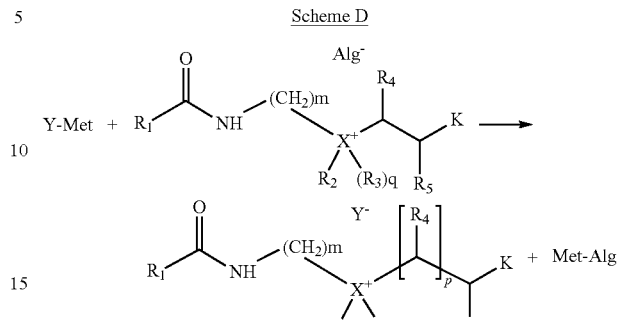

wherein K, $R_1$, $R_2$, $R_3$, $R_4$, $R_5$, X, Z, m, p, q and s have the meanings defined above and Y represents the acid residue which acts as counterion of the final product.

Alternatively, the quaternary salts having formula (I), for Y different from $HCO_3^-$, can be easily obtained by the appropriate molar salification of the acid YH with the bicarbonates of the relative quaternary cations, according to the reaction scheme E:

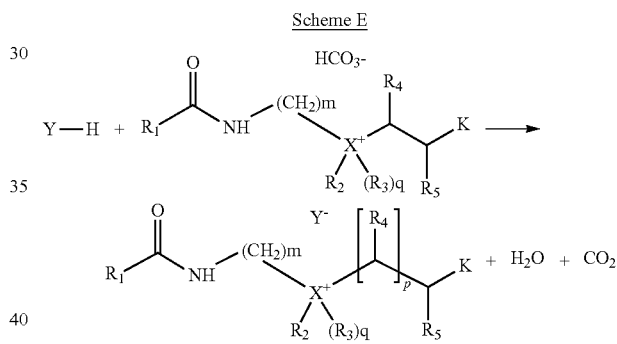

wherein K, $R_1$, $R_2$, $R_3$, $R_4$, $R_5$, X, Z, m, p, q and s have the meanings defined above and Y represents the acid residue which becomes the counterion of the final product.

The reactions can be conveniently carried out in an aqueous or inert organic solvent, at a temperature ranging from room temperature to the boiling point of the reaction mixture, optionally in the presence of an inorganic or organic base.

Examples of preferred solvents for effecting the reaction are ethers (ethyl ether, isopropyl ether, tetrahydrofuran, dioxane, dimethoxyethane, etc.); esters (ethyl acetate, etc.); chlorinated hydrocarbons (methylene chloride, dichloroethane, chloroform, carbon tetrachloride, etc.); aromatic hydrocarbons (benzene, toluene, xylene, etc.); aliphatic hydrocarbons (hexane, heptane, cyclohexane, etc.); aprotic dipolar solvents (N,N-dimethylformamide, dimethylsulfoxide, sulfolane, etc.).

Examples of preferred inorganic bases are: hydroxides, carbonates of alkaline or alkaline earth metals (sodium, potassium, calcium, etc.).

Examples of preferred organic bases are: pyridine, dimethylaminopyridine, aliphatic amines (triethylamine, etc.), cyclic amines (morpholine, piperidine, etc.).

If the substituents $R_1$, $R_2$, $R_3$, $R_4$, $R_5$ contain optic or geometric isomerism centres, the compounds having general formula (I) can be present in all possible configurational isomeric forms.

The scope of the present invention therefore also comprises the use of the compounds having general formula (I) as isomeric mixtures in any proportion, and also the formation and use of the single isomers for the control of phytopathogen fungi in the agronomical field.

When deriving from natural extracts, the compounds having general formula (I) can also be present in mixtures of their homologous products and the scope of the present invention consequently also includes the use of the compounds having general formula (I) as mixtures of their homologous products in any proportion, for the control of phytopathogen fungi and bacteria in the agronomical field.

The compounds having general formula (I) can also be present in a hydrated form by the coordination of any number of water molecules, or obtained in aqueous solution and used directly for agronomical purposes.

The quaternary salts having general formula (I) can also contain and possibly coordinate within their structure other metallic cations, such as for example sodium, potassium, whose number can vary in relation to the preparation method used for the synthesis of the compound having general formula (I).

The scope of the present invention therefore also comprises the use of said solutions of quaternary salts having formula (I), containing said salts for the control of phytopathogen fungi and bacteria in the agronomical field.

The scope of the present invention also comprises the use of mixtures of compounds having general formula (I) in any proportion.

The Applicant has also found, in agronomical practice, that the fungicidal action of the compounds having general formula (I) is particularly effective when combined with that of numerous other fungicidal active principles, thus forming an excellent instrument for antiresistance strategies, allowing the application dosages to be further lowered and stimulating the natural defenses of plants.

The Applicant has again surprisingly found that the compounds having general formula (I), when q has the value of 0 for X=nitrogen, are of particular interest as they are capable of exerting a considerable synergic effect if used in a mixture with Fosetyl-Aluminium (fungicidal active principle corresponding to aluminium triethylphosphonate, described in "The Pesticide Manual", 1994, $X^a$ edition, British Crop Protection Council Ed., page. 530 and more commonly known with the trade-name of Aliette) thus allowing, when applied together, a higher fungicidal activity to be obtained with respect to that envisaged on the basis of the activity of the single components, and also providing excellent antiresistance properties.

An object of the present invention therefore also relates to fungicidal compositions comprising one or more compounds having general formula (I), when q has the value of 0 for X=nitrogen, mixed with Fosetyl-Aluminium (Fosetyl-Al).

Preferred fungicidal compositions are:
a). N,N-dimethylethanolamine and Fosetyl-Al;
b). 3-dimethylamine-1-propanol and Fosetyl-Al;
c). N-ethyl,N-methylethanolamine and Fosetyl-Al;
d). 2-dimethylaminopropanol and Fosetyl-Al;
e). N-lauryl,N-methylethanolamine and Fosetyl-Al;
f). methyl ester of N,N-dimethyl-β-alanine and Fosetyl-Al;
g). methyl ester of N,N-dimethylglycine and Fosetyl-Al.

Composition a) is particularly preferred for its fungicidal activity.

The additional compounds having a fungicidal activity which can be used together with the compounds having general formula (I), when q has the value of 0 for X=sulfur and the value of 1 for X=nitrogen, according to the present invention, are preferably selected from:

(1) IR5885, a dipeptide compound corresponding to diastereoisomeric mixtures of methyl[S-(R,S)]-[3-(N-isopropoxycarbonylvalinyl)-amino]-3-(4-chlorophenyl)propanoate in any proportion, or to one of the two diastereoisomeric forms S-R or S-S taken individually;

(2) IR6141, corresponding to methyl N-(phenylacetyl)-N-2,6-xylyl-R-alaninate;

(3) Tetraconazole (in its racemic form or as an optically active R isomer)

(4) Salicylic acid (SA) or its derivatives such as acetylsalicylic acid (ASA), copper salts of salicylic acid ($SA_2Cu$) or (SACu) or acetylsalicylic acid ($ASA_2Cu$);

(5) A copper (I) or copper (II) salt, such as copper oxychloride, copper hydroxide, Bordeaux mixture, copper sulfate, or a mixture of copper hydroxide and oxychloride (Airone);

(6) Benalaxyl corresponding to methyl N-(phenylacetyl)-N-2,6-xylyl-RS-alaninate;

(7) Metalaxyl corresponding to methyl N-(2-methoxyacetyl)-N-2,6-xylyl-RS-alaninate;

(8) Metalaxyl-M corresponding to methyl N-(2-methoxyacetyl)-N-2,6-xylyl-R-alaninate;

(9) Oxadixyl corresponding to 2-methoxy-N-(2-oxo-1,3-oxazolidin-3-yl)aceto-2',6'-xylidide;

(10) Mandipropamid corresponding to 2-(4-chlorophenyl)-N-[2-(3-methoxy-4-prop-2-inyloxy-phenyl)ethyl]-2-prop-2-inylooxy-acetamide;

(11) Iprovalicarb corresponding to O-(1-methyl-ethyl)-N-[2-methyl-1-[[[1-(4-methyl-phenyl)ethyl]amino]carbonyl]propyl]carbamate;

(12) Benthiavalicarb-isopropyl corresponding to O-isopropyl [(S)-1-{[(1R)-1-(6-fluoro-1,3-benzothiazol-2-yl)ethyl]-carbamoyl-2-methylpropyl]-carbamate;

(13) Cymoxanil corresponding to 1-(2-cyano-2-methoxyimino-acetyl)-3-ethylurea;

(14) Azoxystrobin corresponding to methyl(E)-2-[2-[6-(2-cyanophenoxy)-pyrimidin-4-yloxy]phenyl-3-methoxyacrylate;

(15) Metominofen corresponding to N-methyl-(E)-methoxyimino-(2-phenoxyphenyl)acetamide;

(16) Pyraclostrobin corresponding to methyl N-(2-[1-(4-chlorophenyl)pyrazol-3-yloxymethyl]-phenyl)-N-methoxycarbamate;

(17) Acibenzolar-S-methyl corresponding to methyl benzo(1,2,3)thiadiazole-7-thiocarboxylate;

(18) Famoxadone corresponding to 5-methyl-5-(4-phenoxyphenyl)-3-(phenylamino)oxazolidin-2,4-dione;

(19) Fenamidone corresponding to 4-methyl-4-phenyl-1-(phenylamino)-2-methylthioimidazolidin-5-one;

(20) Cyazofamide, corresponding to 2-cyano-4-chloro-5-(4-methylphenyl)-1-(N,N-dimethylaminosulfamoyl)-imidazole;

(21) Fluazinam corresponding to 3-chloro-N-(3-chloro-5-trifluoromethyl-2-pyridyl)-α-α-α-trifluoro-2,6-dinitro-ρ-toluidine;

(22) Dimethomorph corresponding to (E,Z)-4-[3-(4-chlorophenyl)-3-(3,4-dimethoxyphenyl)-acryloyl]morpholine; or Flumorph (SYP-L190) corresponding to (E,Z)-4-[3-(4-fluorophenyl)-3-(3,4-dimethoxyphenyl)acryloyl]morpholine;

(23) Flumetover corresponding to N,N-diethylamide of 4-trifluoromethyl-6-3,4-dimethoxyphenyl)-benzoic acid;

(24) Chlorothalonil corresponding to 1,3-dicyano-2,4,5-tetrachlorobenzene;

(25) Mancozeb corresponding to the manganese and zinc salt of ethylenebis(dithiocarbamate) (polymer);
(26) Tolylfluanide corresponding to N-dichlorofluoromethylthio-N',N'-dimethyl-N-p-tolylsulfamide;
(27) Folpet corresponding to N-(trichloromethylthio)phthalimide;
(28) Etridiazole corresponding to ethyl-3-trichloromethyl-1,2,4-thiadiazolyl ether;
(29) Hymexanol corresponding to 5-methyliso-oxazol-3-ol;
(30) Propamocarb corresponding to propyl-(3-dimethylaminopropyl)carbamate;
(31) R-3-aminobutanoic acid or RS-3-aminobutanoic acid;
(32) Zoxamide, corresponding to 3,5-dichloro-N-(3-chloro-1-ethyl-1-methyl-2-oxopropyl)-p-toluamide;
(33) Ethaboxam, corresponding to (RS)-(α-cyano-2-thienyl)-4-ethyl-2(ethylamino)-5-thiazolecarboxyamide;
(34) Fluopicolide, corresponding to 2,6-dichloro-N-[3-chloro-5-(trifluoromethyl)-2-pyridylmethyl]benzamide;
(35) Fosetyl, corresponding to ethyl hydrogenphosphonate;
(36) Fosetyl-Al, corresponding to aluminium triethylphosphonate, more commonly known under the trade-name of Aliette.

The compounds (1) are described in Italian patent application Nr. MI98A002583.

Compound (2) is described in patent application WO 98/26654 A2.

Compound (3) is described in "The Pesticide Manual", 1997, XI$^a$ edition, British Crop Protection Council Ed., page 1174.

The compounds (4) are commercial products and their copper salts are described in Italian patent application Nr. MI2001A002430.

The compounds (5) are easily available on the market.

Compound (6) is described in "The Pesticide Manual", 1983, VIIth edition, British Crop Protection Council Ed., page 32.

Compound (7) is described in English patent GB 1,500,581.

Compound (8) is described in patent application WO 96/01559 A1.

Compound (9) is described in English patent GB 2,058,059.

Compound (10) is described in patent application WO 01/87822.

Compound (11) is described in patent application EP 550,788 and EP 775,696.

Compound (12) is described in patent application EP 775,696.

Compound (13) is described in "The Pesticide Manual", 1983, VIIth edition, British Crop Protection Council Ed., page 148.

Compound (14) is described in European patent application EP 382,375.

Compound (15), corresponding to the experimental abbreviation SSF-126, is described in American patent application U.S. Pat. No. 5,185,242.

Compound (16) is described in patent application WO 96/01258.

Compound (17) is described in American patent application U.S. Pat. No. 4,931,581.

Compound (18) is described in "Brighton Crop Protection Conference—Pests and Diseases" 1996, Congress Records.

Compound (19) is described in European patent application EP 629,616.

Compound (20), also called IKF916, is described in European patent application EP 705,823.

Compound (21) is described in European patent application EP 31,257.

The compounds (22) are described respectively in European patent application EP 219,756 and in "Brighton Crop Protection Conference—Pests and Diseases" 2000, Congress Records.

Compound (23) is described in European patent applications EP 360,701 and EP 611,232.

Compound (24) is described in "The Pesticide Manual", 1983, VIIth edition, British Crop Protection Council Ed., page 120.

Compound (25) is described in "The Pesticide Manual", 1983, VIIth edition, British Crop Protection Council Ed., page 339.

Compound (26) is described in "The Pesticide Manual", 1983, VIIth edition, British Crop Protection Council Ed., page 537.

Compound (27) is described in "The Pesticide Manual", 1983, VIIth edition, British Crop Protection Council Ed., page 599.

Compound (28) is described in "The Pesticide Manual", 1983, VIIth edition, British Crop Protection Council Ed., page 252.

Compound (29) is described in "The Pesticide Manual", 1983, VIIth edition, British Crop Protection Council Ed., page 314.

Compound (30) is described in "The Pesticide Manual", 1983, VIIth edition, British Crop Protection Council Ed., page 471.

Compound (31) is described in European patent application EP 753,258.

Compound (32) is described in "Brighton Crop Protection Conference—Pests and Diseases" 1998, Congress Records.

Compound (33) is described in "The Pesticide Manual", 2003, XIII$^a$ edition, British Crop Protection Council Ed.

Compound (34) is described in patent application WO 200111966.

The compounds (35) and (36) are described in "The Pesticide Manual", 1994, X$^a$ edition, British Crop Protection Council Ed., page 530.

A further object of the present invention therefore relates to fungicidal compositions comprising one or more quaternary salts having general formula (I), for q which has the value of 0 for X=sulfur and the value of 1 for X=nitrogen, and fungicidal compositions also containing other active principles.

Preferred fungicidal compositions according to the present invention can be selected from:
1. Acid choline phosphite and IR5885
2. Neutral choline phosphite and IR5885
3. Choline ethylphosphonate and IR5885
4. Choline ethylphosphonate and IR6141
5. Acid choline phosphite and IR6141
6. Neutral choline phosphite and IR6141
7. Acid choline phosphite and Benthiavalicarbisopropyl;
8. Neutral choline phosphite and Benthiavalicarbisopropyl;
9. Acid choline phosphite and ASA$_2$Cu;
10. Acid choline phosphite and SA$_2$CU;
11. Acid choline phosphite and SACu;
12. Neutral choline phosphite and ASA$_2$Cu;
13. Neutral choline phosphite and SA$_2$Cu;
14. Neutral choline phosphite and SACu;
15. Acid laurylcholine phosphite and IR5885;
16. Neutral laurylcholine phosphite and IR5885;
17. Acid laurylcholine phosphite and IR6141;
18. Neutral laurylcholine phosphite and IR6141;
19. Acid choline phosphite and iprovalicarb;

20. Neutral choline phosphite and iprovalicarb;
21. Acid cocamidopropylcholine phosphite and IR5885;
22. Neutral cocamidopropylcholine phosphite and IR5885;
23. Acid cocamidopropylcholine phosphite and IR6141;
24. Neutral cocamidopropylcholine phosphite and IR6141;
25. Acid cocamidopropylcholine phosphite and copper oxychloride;
26. Neutral cocamidopropylcholine phosphite and copper oxychloride;
27. Acid phosphite of the methyl ester of cocamidopropylbetaine and IR5885;
28. Neutral phosphite of the methyl ester of cocami dopropylbetaine and IR5885;
29. Acid phosphite of the methyl ester of cocamidopropylbetaine and IR6141;
30. Neutral phosphite of the methyl ester of cocamidopropylbetaine and IR6141;
31. Acid phosphite of the methyl ester of cocamidopropylbetaine and Airone;
32. Neutral phosphite of the methyl ester of cocamidopropylbetaine and Airone;
33. Choline salicylate and IR5885;
34. Choline acetylsalicylate and IR5885;
35. Choline saccharinate and IR5885;
36. Choline bicarbonate and IR5885;
37. Acid choline phosphite and Mandipropamid;
38. Neutral choline phosphite and Mandipropamid;
39. Acid choline phosphite and copper oxychloride;
40. Neutral choline phosphite and copper oxychloride;
41. Acid choline phosphite and Airone;
42. Neutral choline phosphite and Airone;
43. Acid choline phosphite and Ethaboxam;
44. Neutral choline phosphite and Ethaboxam;
45. Choline bicarbonate and Fosetyl-Al;
46. Choline chloride and Fosetyl-Al;
47. Choline salicylate and Fosetyl-Al;
48. Choline acetylsalicylate and Fosetyl-Al;
49. Cocamidopropylcholine chloride and Fosetyl-Al;
50. Laurylcholine chloride and Fosetyl-Al;
51. Choline bicarbonate and Fosetyl;
52. Choline chloride and Fosetyl.

Particularly preferred are the compositions defined with the following numbers: 1., 2., 3., 4., 5., 6., 7., 8., 9., 10., 11., 12., 13., 19., 20., 33., 34., 35., 36., 45., 46., 52.

A further object of the present invention therefore relates to the use of fungicidal compositions comprising a compound having general formula (I), when q has the value of 0 for X=nitrogen, and the fungicidal compound (36).

Another object of the present invention relates to the use of fungicidal compositions comprising one or more compounds having general formula (I), when q has the value of 0 for X=sulfur and the value of 1 for X=nitrogen, and one or more fungicidal compounds, in particular one or more fungicidal compounds (1)-(36), even more in particular compounds (1), (2), (4), (5), (35) and (36), for the control of phytopathogen fungi.

An object of the present invention also relates to a method for the control of phytopathogen fungi in agricultural crops by the application of the compounds having general formula (I) or fungicidal compositions comprising one or more compounds having general formula (I) and one or more fungicidal compounds, in particular one or more fungicidal compounds (1)-(36), even more in particular compounds (1), (2), (4), (5), (35) e (36), for the control of phytopathogen fungi.

Examples of phytopathogen fungi and bacteria controlled by the above compounds having general formula (I) and by the above compositions, together with examples of application crops, are indicated below for purely illustrative and non-limiting purposes:

*Helminthosporium* spp on cereals;
*Erysiphe* spp on cereals;
*Puccinia* spp. on cereals;
*Plasmopara viticola* on vines;
*Pythium* spp on vegetables;
*Phytophthora* spp. on vegetables;
*Rhynchosporium* on cereals;
*Septoria* spp. on cereals;
*Sphaerotheca fuliginea* on cucurbits (for example cucumbers);
*Podosphaera leucotricha* on apple trees;
*Pyricularia oryzae* on rice;
*Uncinula necator* on vines;
*Venturia* spp. on fruit trees;
*Botrytis cinerea* on vines and vegetables;
*Fusarium* spp. on cereals;
*Alternaria* spp. on fruit trees and vegetables;
*Cercospora* spp. on sugar beet;
*Xantomonas*;
*Bacillus* spp.

The compounds having general formula (I) and mixtures thereof with one or more fungicidal compounds are capable of exerting a bactericidal/fungicidal action of both a curative and preventive nature and have a low or zero phytotoxicity.

A further object of the present invention therefore relates to a method for the control of phytopathogen fungi and bacteria in agricultural crops by the application of the compounds having general formula (I) having a direct fungicidal and bactericidal activity and a method for the stimulation of the natural defense systems of plants from abiotic stress (temperature, salinity, drought, etc.) and biotic stress and the induction of resistance in the plants themselves by the application of the compounds having general formula (I).

The quantity of compound to be applied for obtaining the desired effect can vary in relation to various factors such as, for example, the compound used, the crop to be preserved, the type of pathogen, the degree of infection, the climatic conditions, the application method and the formulation adopted.

Doses of compound ranging from 10 g to 5 kg per hectare generally provide a sufficient control.

For practical uses in agriculture it is often convenient to apply fungicidal compositions containing one or more compounds having general formula (I).

The application of these compositions can be effected on all parts of the plant, for example on the leaves, stems, branches and roots, or on the seeds themselves before sowing, or on the ground in which the plant grows.

Compositions can be used in the form of dry powders, wettable powders, emulsifying concentrates, microemulsions, pastes, granulates, solutions, suspensions, etc.: the choice of the type of formulation will depend on the specific use.

The compositions are prepared in the known way, for example by diluting or dissolving the active substance with a solvent medium and/or a solid diluent, possibly in the presence of surface-active agents.

Solid diluents or supports which can be used are, for example: silica, kaolin, bentonite, talc, infusorial earth, dolomite, calcium carbonate, magnesia, gypsum, clays, synthetic silicates, attapulgite, sepiolite.

Liquid diluents which can be used, are for example, in addition to water, aromatic organic solvents (xylols or alkyl benzol mixtures, chlorobenzene, etc.), paraffins (oil fractions), alcohols (methanol, propanol, butanol, octanol, glycerin, etc.), esters (ethyl acetate, isobutyl acetate, etc.), ketones (cyclohexanone, acetone, acetophenone, isophorone, ethylamylketone, etc.), amides (N,N-dimethylformamide, N-methylpyrrolidone, etc.).

Surface-active agents which can be used are salts of sodium, calcium, triethylamine or triethanolamine, alkylsulfonates, alkylaryl-sulfonates, polyethoxylated alkylphenols, polyethoxylated esters of sorbitol, ligninsulfonates, etc.

The compositions can also contain special additives for particular purposes, for example adhesion agents such as gum arabic, polyvinyl alcohol, polyvinylpyrrolidone, polyacrylates, etc.

In the fungicidal compositions, object of the present invention, the concentration of active substances varies from 0.1% to 98% by weight, preferably from 0.5 to 90% by weight.

If desired, it is possible to also add compatible active principles to the compositions, object of the present invention, such as, for example, phyto-regulators, antibiotics, herbicides, insecticides, fertilizers.

The following examples are provided for a better understanding of the invention for illustrative and non-limiting purposes of the present invention.

EXAMPLE 1

Preparation of Neutral Choline Phosphite
(Compound 1)

A solution of 16.10 g of potash in 20 ml of water is added dropwise under cooling to a solution of 10 g of phosphorous acid in 5 ml of water.

The mixture is kept under stirring at room temperature and 34.07 g of choline chloride are added in portions.

At the end of the addition, the mixture is left under stirring for 3 hours and the solution thus obtained is used as such.

EXAMPLE 2

Preparation of Acid Choline Phosphite
(Compound 2)

20.15 g of choline bicarbonate are added in portions, under cooling, to a solution of 10 g of phosphorous acid in 3 ml of water.

At the end of the addition, the mixture is left under stirring for 4 hours and the solution thus obtained is used as such.

EXAMPLE 3

Preparation of Cholesterylcarbonylamidopropyldimethylamine 3.41 g of 3-dimethylamino-1-propylamine are added to a solution of 15 g of cholesterylchloroformiate in 70 ml of methylene chloride and 3.49 ml of triethylamine. The moisture is kept under stirring at room temperature for a night. The product obtained is extracted, washed with water, anhydrified with $Na_2SO_4$ obtaining, after drying, 15.8 g of the desired compound (yield: 92%).

Elemental analysis [% found (theoretical)]=C, 77.0; (76.8); H, 11.9; (11.2); N, 5.1; (5.4).

EXAMPLE 4

Preparation of Cholesterylcarbonylamidopropylcholine Chloride
(Compound 3)

12 g of cholesterylcarbonylamidopropyldimethylamine in 32 ml of water are charged into a reactor and 1.9 g of 2-chloroethanol are added. The reaction mixture is slowly heated to 98° C. After about 5 hours, the starting products are completely used up and the solution obtained is used as such.

EXAMPLE 5

Preparation of Neutral Cholesterylcarbonylamidopropylcholine Phosphite
(Compound 4)

A solution of 3.22 g of potash in 4 ml of water is added dropwise, under cooling, to a solution of 2 g of phosphorous acid in 2 ml of water.

The mixture is maintained under stirring at room temperature and 28.9 g of cholesterylcarbonylamidopropylcholine chloride are added.

At the end of the addition the mixture is left under stirring for 3 hours, and the solution thus obtained is used as such.

EXAMPLE 6

Preparation of Acid Cholesterylcarbonylamidopropylcholine Phosphite
(Compound 5)

A solution of 1.61 g of potash in 2 ml of water is added dropwise, under cooling to a solution of 2 g of phosphorous acid in 2 ml of water.

The mixture is maintained under stirring at room temperature and 14.45 g of cholesterylcarbonylamidopropylcholine chloride are added.

At the end of the addition the mixture is left under stirring for 3 hours, and the solution thus obtained is used as such.

The following compounds were prepared analogously to what is described in the examples:

TABLE 1

| Number | Compound |
|---|---|
| 6 | Acid laurylcholine phosphite |
| 7 | Neutral laurylcholine phosphite |
| 8 | Acid cocamidopropylcholine phosphite |
| 9 | Neutral cocamidopropylcholine phosphite |
| 10 | Acid stearylcholine phosphite |
| 11 | Neutral stearylcholine phosphite |
| 12 | Acid N,N-dimethyl,N-laurylamidopropyl[L]valinol phosphite |
| 13 | Neutral N,N-dimethyl,N-laurylamidopropyl-[L]valinol phosphite |
| 14 | Choline salicylate |
| 15 | Choline acetylsalicylate |
| 16 | Choline saccharinate |
| 17 | Choline cyclamate |
| 18 | Choline taurinate |
| 19 | Choline sulfate |
| 20 | Acid choline phosphate |
| 21 | Neutral choline phosphate |
| 22 | Laurylcholine salicylate |
| 23 | Laurylcholine acetylsalicylate |
| 24 | Laurylcholine saccharinate |
| 25 | Laurylcholine cyclamate |
| 26 | Laurylcholine taurinate |
| 27 | Cocamidopropylcholine salicylate |
| 28 | Cocamidopropylcholine acetylsalicylate |
| 29 | Cocamidopropylcholine saccharinate |
| 30 | Cocamidopropylcholine cyclamate |
| 31 | Cocamidopropylcholine taurinate |
| 32 | Acid phosphite of the methyl ester of cocamidopropylbetaine |
| 33 | Neutral phosphite of the methyl ester of cocamidopropylbetaine |
| 34 | Acid phosphate of the methyl ester of cocamidopropylbetaine |
| 35 | Neutral phosphate of the methyl ester of cocamidopropylbetaine |
| 36 | Bicarbonate of the methyl ester of cocamidopropylbetaine |

TABLE 1-continued

| Number | Compound |
|---|---|
| 37 | Salicylate of the methyl ester of cocamidopropyl-betaine |
| 38 | Saccharinate of the methyl ester of cocamidopropylbetaine |
| 39 | Acid phosphite of the cetyl ester of cocamidopropylbetaine |
| 40 | Neutral phosphite of the cetyl ester of cocamidopropylbetaine |
| 41 | Salicylate of the cetyl ester of cocamidopropyl-betaine |
| 42 | Saccharinate of the cetyl ester of cocamidopropylbetaine |
| 43 | Acetylsalicylate of the cetyl ester of cocamidopropylbetaine |
| 44 | Cyclamate of the cetyl ester of cocamidopropylbetaine |
| 45 | Acid phosphite of the methyl ester of carnitine |
| 46 | Neutral phosphite of the methyl ester of carnitine |
| 47 | Salicylate of the methyl ester of carnitine |
| 48 | Acetylsalicylate of the methyl ester of carnitine |
| 49 | Saccharinate of the methyl ester of carnitine |
| 50 | Choline ethylphosphonate |
| 51 | Laurylcholine ethylphosphonate |
| 52 | Cocamidopropylcholine ethylphosphonate |

EXAMPLE 7

Determination of the Fungicidal Activity Against Peronospora of Vines (*Plasmopara viticola*). Table 2

Vine leaves (cultivar Dolcetto), grown in vases in a conditioned environment (20±1° C., 70% relative humidity) are treated by spraying both sides of the leaves with compounds 1 and 2, dispersed in a hydroacetone solution at 20% by volume in acetone.

After remaining 24 hours in a conditioned environment, the plants were sprayed on both sides of the leaves with an aqueous suspension of conidia of *Plasmopara viticola* (20,000 conidia per cm$^3$).

The plants are kept in a humidity saturated environment at 21° C. for the incubation period of the fungus.

At the end of this period (7 days), the fungicidal activity is evaluated according to an evaluation percentage scale from 0 (completely infected plant) to 100 (healthy plant).

TABLE 2

7-day preventive activity on *Plasmopara viticola* of the compounds having general formula (I)

| Compound N° | Activity 1000 ppm* | Activity 500 ppm* |
|---|---|---|
| 1 (neutral choline phosphite) | 100 | 90 |
| 2 (acid choline phosphite) | 95 | 85 |
| K$_2$HPO$_3$ | 80 | 45 |
| Choline chloride | 57 | 35 |
| Choline bicarbonate | 84 | 75 |

*the doses in ppm refer to the quantity of equivalent phosphorous acid.

EXAMPLE 8

Determination of the Fungicidal Activity Against Peronospora of Potatoes (*Phytophtora infestans*). Table 3

Leaves of potato plants, Primura variety, grown in vases in a conditioned environment (20±1° C., 70% relative humidity) were infected with an aqueous suspension of spores of *Phytophthora infestans* (100,000 spores per cm$^3$).

After remaining 24 hours in a conditioned environment, both sides of the leaves were sprayed with the products under examination dissolved in a hydroacetone solution at 20% of acetone (vol./vol.).

After drying, the plants were transferred for the incubation period of the fungus (4 days) in a conditioned environment at 70% of relative humidity and 24° C.

The intensity of the disease was finally evaluated according to an evaluation percentage scale from 100 (healthy plant) to 0 (completely infected plant).

TABLE 3

1-day curative activity on *Phytophthora infestans* of the compounds having general formula (I)

| Compound | Activity |
|---|---|
| Choline chloride | 15 (2690 ppm*) |
| K$_2$HPO$_3$ | 40 (1575 ppm**) |
| 2(acid choline phosphite) | 65 (1575 ppm**) |

*the dose in ppm refers to the quantity of choline contained in Compound N° 2
**the doses in ppm refer to the quantity of equivalent phosphorous acid.

From the data indicated in Table 3, it is possible to assert the synergic effect of the ionic couple present in Compound Nr. 2.

When in fact the fungicidal activity found experimentally (65) is greater than that expected (49), calculated considering the contribution of potassium phosphite and choline chloride and using the Limpel formula ("Pesticide Science" (1987), vol. 19, pages 309-315), then this activity should be considered as being a synergic effect with a synergy factor equal to 1.4 (experimental activity/activity calculated according to Limpel).

EXAMPLE 9

Determination of the Fungicidal Activity of Fungicidal Mixtures Against Peronospora of Potatoes (*Phytophtora infestans*). Tables 4-6

Leaves of potato plants, Primura variety, grown in vases in a conditioned environment (20±1° C., 70% relative humidity) were infected with an aqueous suspension of spores of *Phytophthora infestans* (100,000 spores per cm$^3$).

After remaining 24 hours in a conditioned environment, both sides of the leaves were sprayed with the fungicidal mixtures under examination dissolved in a hydroacetone solution at 20% of acetone (vol./vol.).

After drying, the plants were transferred for the incubation period of the fungus (4 days) in a conditioned environment at 70% of relative humidity and 24° C.

The intensity of the disease was finally evaluated according to an evaluation percentage scale from 100 (healthy plant) to 0 (completely infected plant).

From the data indicated in tables 4-6, it is possible to assert the synergic effect of the mixtures, consisting of the mixtures under examination, compared with the efficacy expected using the Limpel formula ("Pesticide Science" (1987), vol. 19, pages 309-315):

$$E=x+y-(xy/100)$$

wherein:
E is the fungicidal activity expected, without synergic effects, from a mixture obtained by mixing g.x of compound X with g.y of compound Y;
x is the activity of compound X when used alone at a dose of g.x;

y is the activity of compound Y when used alone at a dose of g.y.

When the fungicidal activity found experimentally is greater than the value of E, this activity should be considered a synergic effect.

TABLE 4

1-day curative activity on *Phytophthora infestans* of the fungicidal mixtures consisting of Fosetyl-Al which at 1600 ppm* (g · x) is 0 (x) with compounds having general formula (I) when q has the value of 0 for X = nitrogen.

| Mixture | Dose ppm (g · y) | Activity (y) | Activity mixture according to Limpel (E) | Experimental activity of mixture | Synergy factor |
|---|---|---|---|---|---|
| Mixture 1. (N,N-dimethyl-ethanolamine and Fosetyl-Al) | 1736 | 30 | 30 | 90 | 3 |
| Mixture 2. (3-dimethylamine-1-propanol and Fosetyl-Al | 1745 | 25 | 25 | 65 | 2.6 |

*the doses in ppm refer to the quantity of equivalent phosphorous acid.

TABLE 5

1-day curative activity on *Phytophthora infestans* of fungicidal mixtures consisting of IR5885 which at 150 ppm (g · x) is 15 (x) with compounds having general formula (I) when q has the value of 0 for X = sulfur and the value of 1 for X = nitrogen.

| Mixture | Dose ppm* (g · y) | Activity (y) | Activity of mixture according to Limpel (E) | Experimental activity of mixture | Synergy factor |
|---|---|---|---|---|---|
| Mixture 3. (IR5885 and acid choline phosphite, compound 1) | 1575 | 65 | 70.25 | 98 | 1.4 |
| Mixture 4. (IR5885 and neutral choline phosphite, compound 2) | 1575 | 65 | 70.25 | 90 | 1.3 |

*the doses in ppm refer to the quantity of equivalent phosphorous acid.

TABLE 6

1-day curative activity on *Phytophthora infestans* of fungicidal mixtures consisting of Fosetyl-Al which at 1600 ppm* (g · x) is 0 (x) with other compounds having general formula (I) when q has the meaning of 0 for X = sulfur and the value of 1 for X = nitrogen.

| Mixture | Dose ppm (g · y) | Activity (y) | Activity of mixture according to Limpel (E) | Experimental activity of mixture | Synergy factor |
|---|---|---|---|---|---|
| Mixture 5. (Choline chloride and Fosetyl-Al) | 2730 | 20 | 70.25 | 75 | 1.4 |

*the doses in ppm refer to the quantity of equivalent phosphorous acid.

EXAMPLE 10

Determination of the Fungicidal Activity of Fungicidal Mixtures Against Peronospora of Vines (*Plasmopara viticola*). Table 7

Leaves of vines (cultivar Dolcetto), grown in vases in a conditioned environment (20±1° C.), 70% relative humidity) were infected with an aqueous suspension of spores of *Plasmopara viticola* (200,000 conidia per cm$^3$).

After remaining 24 hours in a conditioned environment, both sides of the leaves were sprayed with the fungicidal mixtures under examination dissolved in a hydroacetone solution at 20% of acetone (vol./vol.).

After drying, the plants were transferred for the incubation period of the fungus (6 days) to a conditioned at 70% relative humidity and 24° C.

At the end of this period (7 days), the fungicidal activity is evaluated according to an evaluation percentage scale from 0 (completely infected plant) to 100 (healthy plant).

From the data indicated in table 7, it is possible to assert the synergic effect of the mixtures under examination, compared with the expected efficacy using the Limpel formula already described in example 9.

TABLE 7

1-day curative activity on *Plasmopara viticola* of fungicidal mixtures consisting of Fosetyl-Al which at 1200 ppm* (g · x) is 23 (x) with other compounds having general formula (I).

| Mixture | Dose ppm (g · y) | Activity (y) | Activity of mixture according to Limpel (E) | Experimental activity of mixture | Synergy factor |
|---|---|---|---|---|---|
| Mixture 1. (N,N-dimethyl-ethanolamina and Fosetyl-Al) | 1302 | 25 | 42.25 | 100 | 2.4 |
| Mixture 5. (Choline chloride and Fosetyl-Al) | 2047 | 20 | 34.4 | 100 | 2.9 |

*the doses in ppm refer to the quantity of equivalent phosphorous acid.

EXAMPLE 11

Determination of the Fungicidal Activity of Fungicidal Mixtures Against Peronospora of Tobacco (*Plasmopara tabacina*). Table 8

Leaves of tobacco plants (cultivar Barley), grown in vases in a conditioned environment (20±1° C.), 70% relative humidity) were infected with an aqueous solution of spores of *Plasmopara tabacina* (200,000 conidia per cm$^3$).

After remaining 24 hours in a conditioned environment, both sides of the leaves were sprayed with the fungicidal mixtures under examination dissolved in a hydroacetone solution at 20% of acetone (vol./vol.).

After drying, the plants were transferred for the incubation period of the fungus (6 days) to a conditioned environment at 70% relative humidity and 24° C.

At the end of this period (7 days), the fungicidal activity is evaluated according to an evaluation percentage scale from 0 (completely infected plant) to 100 (healthy plant).

From the data indicated in table 8, it is possible to assert the synergic effect of the mixtures under examination, compared with the expected efficacy using the Limpel formula already described in example 9.

TABLE 8

1-day curative activity on *Plasmopara tabacina* of fungicidal mixtures consisting of Fosetyl-Al which at 1200 ppm* (g · $\underline{x}$) is 15 (x) with other compounds having general formula (I).

| Mixture | Dose ppm (g · $\underline{y}$) | Activity (y) | Activity of mixture according to Limpel (E) | Experimental activity of mixture | Synergy factor |
|---|---|---|---|---|---|
| Mixture 1. (N,N-dimethyl-ethanolamina and Fosetyl-Al) | 1302 | 5 | 19 | 100 | 5.3 |
| Mixture 5. (Choline chloride and Fosetyl-Al) | 2047 | 10 | 23.5 | 100 | 4.3 |

*the doses in ppm refer to the quantity of equivalent phosphorous acid.

The invention claimed is:
1. Organic compounds having general formula (I),

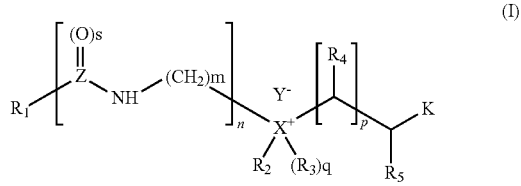

wherein:
K represents a $CH_2OH$ or $COOR_a$ group;
$R_a$ represents a linear or branched $C_1$-$C_{26}$ alkyl group optionally substituted;
$R_1$ represents a hydrogen or a linear or branched $C_1$-$C_{26}$ alkyl group optionally substituted; a linear or branched $C_x$-$C_{26}$ haloalkyl group optionally substituted; a linear or branched $C_1$-$C_{26}$ alkoxy group optionally substituted; a linear or branched $C_1$-$C_{26}$ alkylthio group optionally substituted; a linear or branched $C_2$-$C_{26}$ alkenyl group optionally substituted; a linear or branched $C_2$-$C_{26}$ alkynyl group optionally substituted; a $C_3$-$C_{30}$ cycloalkyl group optionally condensed or a condensed $C_{17}$ cycloalkyl group of the steroid type optionally substituted; a $C_3$-$C_{30}$ cycloalkoxy group optionally condensed and optionally substituted; a heterocyclic group optionally substituted; an aryl group optionally substituted; a heteroaryl group optionally substituted; a linear or cyclic $C_6$-$C_{12}$ group of the saccharide type optionally substituted; a $C_1$-$C_{26}$ alkylamine group or a $C_2$-$C_{26}$ dialkylamine group optionally substituted for n different from 0;
$R_2$ and $R_3$, the same or different, represent a $C_1$-$C_3$ alkyl group optionally substituted;
$R_4$ and $R_5$, the same or different, represent a hydrogen atom, or a linear or branched $C_1$-$C_6$ alkyl group optionally substituted; a linear or branched $C_2$-$C_6$ alkenyl group optionally substituted; a $C_3$-$C_6$ cycloalkyl group optionally substituted; a hydroxyl group; an aryl group optionally substituted; a heteroaryl group optionally substituted; a heterocyclic group optionally substituted;
$R_4$ and $R_5$ can individually form a cycle together with $R_2$;
X represents a nitrogen or sulfur atom;
Z represents a carbon or sulfur atom;
m represents a number ranging from 1 to 5;
n and p represent a number ranging from 0 to 3;
q has the value of 0 for X=sulfur or the value of 1 for nitrogen;
Y represents a phosphite anion $H_2PO_3$.

2. The compounds according to claim 1, characterized in that the $C_1$-$C_{26}$ alkyl group is selected from methyl, ethyl, propyl, isopropyl, butyl, isobutyl, tert-butyl, capiyl, lauryl, stearyl, eicosyl, hexacosyl.

3. The compounds according to claim 1, characterized in that the $C_1$-$C_{26}$ haloalkyl group is selected from fluoromethyl, difluoromethyl, trifluoromethyl, trichloromethyl, 2, 2, 2-trifluorocthyl, 2, 2, 2-trichloroethyl, 2, 2, 3, 3-tetrafluoropropyl, 2, 2 , 3 , 3 , 3-pentafluoropropyl, perfluorooetanyl, perfluorododecyl.

4. The compounds according to claim 1, characterized in that the $C_1$-$C_{26}$ alkoxy group is selected from methoxy, ethoxy, isopropoxy, cyclopropylmethoxy, lauryloxy.

5. The compounds according to claim 1, characterized in that the $C_1$-$C_{26}$ thioalkyl group is selected from thiomethyl, thioethyl, thiolauryl, thiocapryl.

6. The compounds according to claim 1, characterized in that the $C_2$-$C_{26}$ alkenyl group is selected from ethenyl, propenyl, butenyl, 1-decenyl, 8-heptadecenyl, 8,11,14-heptadecatrienyl, 8, 11-heptadecadienyl.

7. The compounds according to claim 1, characterized in that the $C_2$-$C_{26}$ alkynyl group is selected from ethynyl, propargyl, 1-dodecynyl, 1-octadecynyl.

8. The compounds according to claim 1, characterized in that the $C_3$-$C_{30}$ cycloalkyl group optionally condensed is selected from cyclopropyl, 2, 2-diehlorocyclopropyl, cyclobutyl, cyclopentyl, cyclohexyl, decaline, abietyl.

9. The compounds according to claim 1, characterized in that the condensed $C_{17}$ cycloalkyl group of the steroid type is selected from cholanyl, chenodeoxycholanyl , ursodeoxycholanyl, deoxycholanyl, iodeoxycholanyl, lithocholanyl.

10. The compounds according to claim 1, characterized in that the $C_3$-$C_{30}$ cycloalkoxy group is selected from cyclopentoxy, cyclohexyloxy, cholesteryl.

11. The compounds according to claim 1, characterized in that the $C_1$-$C_{26}$ alkylarnine or $C_2$-$C_{26}$ dialkylamine groups are selected from methylamine, dimethylamine, ethylamine, isopropylamine, dibutylamine, dioctylamine, hexadecylaraine, didecylamine.

12. The compounds according to claim 1, characterized in that the aryl group is selected from phenyl, naphthyl, phenanthryl.

13. The compounds according to claim 1, characterized in that the heteroaryl group is selected from pyridine, pyrimidine, pyridazine, pyrazine, triazine, tetrazine, quinoline, quinoxaline, quinazoline, furan, thiophene, pyrol, oxazole, thiazole, isoxazole, isothiazole, oxadiazole, thiadiazale, pyrazole, imidazole, triazole, tetrazole, indole, benzofuran, benzothiophene, benzoxazole, benzothiazole, benzoxadiazole, benzofhiadiazole, benzopyrazole, benzimidazole, benzotriazole, triazolepyridine, triazolepyrimidine, thiazoletriazole, cumarin.

14. The compounds according to claim 1, characterized in that the heterocyclic group is selected from pyrrolidine, piperidine, dihydropyridine, piperazine, 2,6-diketopiperazine, 2-ketoazetidine, morpholine, triazine, indoline.

15. The compounds according to claim 1, characterized in that the linear or cyclic $C_6$-$C_{12}$ group of the saccharide type is selected from gluconyl, glucopyranosyl, β-D-fructofuranosyl-α-D-glueopyranosyl, 4-O-β-D-galactopyranosyl-D-glucosyl.

16. The compounds according to claim 1, characterized in that, they are selected from:
   Acid choline phosphite;
   Acid laurylcholine phosphite;
   Acid cocamidopropylcholine phosphate;
   Acid stearyleholine phosphite;
   Acid cholesterylcarbonylamidopropylcholine phosphite;
   Acid cholanylamidopropylcholine phosphite;
   Acid chenodeoxycholanylamidopropylcholine phosphite;
   Acid N, N-dimethyl, N- laurylamidopropyl [L] valiny phosphite;
   Acid N, N-dimethyl, N-lauryl [L] valiny phosphite;
   Acid N-lauryl, N-methyl [L] 2-pyrrolidineniethanol phosphite;
   Acid phosphite of the methyl ester of cocamidopropylbetaine;
   Acid phosphite of betaine cetyl ester;
   Acid phosphite of the methyl ester of cholanylamidopropylbetaine;
   Acid phosphite of the methyl ester of camitine.

17. The compounds according to claim 1, characterized in that if the substituents $R_1$, $R_2$, $R_3$, $R_4$, $R_5$ contain optic or geometric isomerism centres; they can be present in all possible configurational isomeric forms.

18. A method for the control ofphytopathogenic fungi and bacteria on plants, comprising applyiingto said plants one or more compounds having the general formula (I)

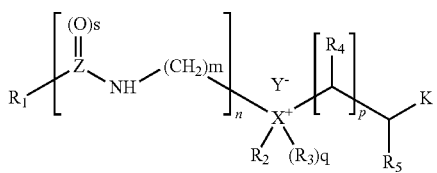

(I)

wherein
   K represents a $CH_2OH$ or $COOR_a$ group;
   $R_a$ represents a linear or branched $C_1$-$C_{26}$ alkyl group optionally substituted;
   $R_1$ represents a hydrogen or a linear or branched $C_1$-$C_{26}$ alkyl group optionally substituted; a linear or branched $C_1$-$C_{26}$ haloalkyl group optionally substituted; a linear or branched $C_1$-$C_{26}$ alkoxy group optionally substituted; a linear or branched $C_1$-$C_{26}$ alkylthio group optionally substituted; a linear or branched $C_2$-$C_{25}$ alkenyl group optionally substituted; a linear or branched $C_2$-$C_{26}$ alkynyl group optionally substituted; a $C_3$-$C_{30}$ cycloalkyl group optionally condensed or a condensed $C_{17}$ cycloalkyl group of the steroid type optionally substituted; a $C_3$-$C_{30}$ cycloalkoxy group optionally condensed and optionally substituted; a heterocyclic group optionally substituted; an aryl group optionally substituted; a heteroaryl group optionally substituted; a linear or cyclic $C_6$-$C_{12}$ group of the saccharide type optionally substituted; a $C_1$-$C_{26}$ alkylamine group or a $C_2$-$C_{26}$ dialkylarnine group optionally substituted for n different from 0;
   $R_2$ and $R_3$, the same or different, represent a $C_1$-$C_3$ alkyl group optionally substituted;
   R4 and $R_5$, the same or different, represent a hydrogen atom, or a linear or branched $C_1$-$C_6$ alkyl group optionally substituted; a linear or branched $C_2$-$C_6$ alkenyl group optionally substituted; a $C_3$-$C_6$ cycloalkyl group optionally substituted; a hydroxyl group; an aryl group optionally substituted; a heteroaryl group optionally substituted; a heterocyclic group optionally substituted; $R_4$ and $R_5$ can individually form a cycle together with $R_2$;
   X represents a nitrogen or sulfur atom;
   Z represents a carbon or sulfur atom;
   m represents a number ranging from 1 to 5;
   n and p represent a number ranging from 0 to 3;
   q has the value of 0 for X=sulfur or the value of 1 for nitrogen;
   Y, represents a phosphie anion $H_2PO_3$.

19. The method according to claim 18 where the compounds ofgeneral formula I are applied to plants for the control of phytopathogenic fungi and bacteria by the stimulation of the natural defense systems of plants from abiotic stress of temperature, of salinity or of drought, and from biotic stress and for the induction of resistance in the plants themselves.

20. The method according to claim 18, characterized in that the compounds of general formula (I) are applied for curative and/or preventive applications.

21. The method according to claim 18 wherein the compounds having general formula (I) are used in a quantity ranging from 10 g to 5 kg per hectare of plants.

22. The method according to claim 18 wherein the compounds having general formula (I) are present as single isomers or as isomeric mixtures in any proportion.

23. The method according to claim 18 wherein the compounds having general. formula I are applied to genetically modified plant varieties.

24. A fungicidal composition comprising one or more of compounds having general formula (I) according to claim 1.

25. The composition according to claim 24, characterized in that it contains other active principles.

26. The composition according to claim 25 characterized in that it contains as further active principles at least one of the following products:
   IR5885, a dipeptide compound corresponding to diastereoisomeric mixtures of methyl [S-(R,S)]-[3-(N-isopropoxycarhooylvalinyl)-amino]-3-(4-chloro-phenylpropanoate in any proportion, or to one of the two diastereoisomeric forms S-R or S-S taken individually;
   IR6141, corresponding to methyl N-(phenylacetyl)-N-2,6-xylyl-R-alaninate;
   salicylic acid (SA.) or its derivatives selected from acetylsalicylic acid (ASA), copper salts of salicylic acid ($SA_2Cu$) or (SACu) or acetylsalicylic acid ($ASA_2Cu$);
   a copper (I) or copper (II) salt, selected from copper oxychloride, copper hydroxide, Bordeaux mixture, copper sulfate, or a mixture of copper hydroxide and oxychloride;
   Fosetyl, corresponding to ethyl hydrogenphosphonate;
   Fosetyl-AI, corresponding to aluminum triethylphos phonate.

27. The composition according to claim 25 characterized in that it is selected from:

Acid choline phosphite and IR5885;
Acid choline phosphate and IR6141;
Acid choline phosphite and Benthiavalicarb-isopropyl;
Acid choline phosphite and $ASA_2Cu$;
Acid choline phosphite and $SA_2Cu$;
Acid choline phosphite and SACu;
Acid choline phosphite and iprovalicarb.

28. The composition according to claim 24 wherein the concentration of active principle ranges from 1% to 90%.

29. The method for the control of phytopathogenic fungi and bacteria on plants comprising applying to said plants a composition according to claim 24.

30. The method according to claim 24, wherein a fungicidal composition is applied to plants for the stimulation of the natural defense systems of plants from abiotic stress and biotic stress and the induction of resistance. in the plants themselves.

31. The method according to claim 29, wherein the application of the composition is effected on all parts of the plant, on the leaves, stems, branches and roots, or OD the seeds themselves before planting, or on the ground in which the plant grows.

32. The composition according to claim 28 wherein the concentration of active principle ranges from 5 to 50%.

* * * * *